US010126459B2

(12) United States Patent
Wurzbach et al.

(10) Patent No.: US 10,126,459 B2
(45) Date of Patent: Nov. 13, 2018

(54) SYSTEM AND METHOD FOR DEPTH PROFILING BY TEMPORAL AND SPATIAL RANGE GATING BASED ON PENETRATING ELECTROMAGNETIC RADIATION

(71) Applicant: Raytheon Company, Waltham, MA (US)

(72) Inventors: James A. Wurzbach, San Diego, CA (US); Kalin Spariosu, Thousand Oaks, CA (US); Bernard Harris, Pelham, MA (US); Eric J. Griffin, Rancho Palos Verdes, CA (US)

(73) Assignee: RAYTHEON COMPANY, Waltham, MA (US)

( * ) Notice: Subject to any disclaimer, the term of this patent is extended or adjusted under 35 U.S.C. 154(b) by 609 days.

(21) Appl. No.: 14/645,666

(22) Filed: Mar. 12, 2015

(65) Prior Publication Data

US 2016/0266273 A1 Sep. 15, 2016

(51) Int. Cl.
*G01V 5/00* (2006.01)
*G01N 23/203* (2006.01)
*G01B 15/04* (2006.01)

(52) U.S. Cl.
CPC ........... *G01V 5/0025* (2013.01); *G01B 15/04* (2013.01); *G01N 23/203* (2013.01)

(58) Field of Classification Search
CPC ........... G01N 23/203; G01N 2223/053; G01N 21/956; G01N 2223/051; G01N 2223/616; G01V 5/0025; G01V 5/0066; G01V 5/12; A61B 6/483
See application file for complete search history.

(56) References Cited

U.S. PATENT DOCUMENTS

| 4,219,812 | A | 8/1980 | Rittenbach |
| 5,164,823 | A | 11/1992 | Keeler |
| 5,457,639 | A | 10/1995 | Ulich et al. |
| 5,541,605 | A | 7/1996 | Heger |
| 5,543,799 | A | 8/1996 | Heger |
| 5,774,091 | A | 6/1998 | McEwan |
| 5,805,110 | A | 9/1998 | McEwan |
| 5,854,603 | A | 12/1998 | Heger |
| 5,896,102 | A | 4/1999 | Heger |
| 2009/0238335 | A1* | 9/2009 | Ripp .................... G01V 5/0008 378/57 |

(Continued)

FOREIGN PATENT DOCUMENTS

| CA | 2353014 A1 | 1/2003 |
| DE | 4205752 A1 | 8/1993 |
| WO | 9933101 A1 | 7/1999 |

*Primary Examiner* — Hoon Song
(74) *Attorney, Agent, or Firm* — Cantor Colburn LLP (57) ABSTRACT

A method, apparatus and system for profiling a material composition of a volume is disclosed. A beam source directs a pulsed beam of electromagnetic energy from into the volume. A plurality of backscattered beams is received at a detector. The plurality of backscattered beams is generated from a plurality of depths within the volume in response to interactions of the directed pulsed beam at the plurality of depths. A processor performs range gating of the plurality of backscattered beams to obtain a depth profile of backscattered intensity within the volume and estimates a material composition at different depths of the volume from the generated depth profile.

20 Claims, 4 Drawing Sheets

(56) References Cited

U.S. PATENT DOCUMENTS

2012/0134473 A1\* 5/2012 Morton ............... G01V 5/0008
378/87
2012/0307230 A1 12/2012 Dorrington et al.

\* cited by examiner

SYSTEM AND METHOD FOR DEPTH PROFILING BY TEMPORAL AND SPATIAL RANGE GATING BASED ON PENETRATING ELECTROMAGNETIC RADIATION

BACKGROUND

The present disclosure relates generally to a method and apparatus for determining a presence of a concealed object and, in particular, to a method of determining the presence of the concealed object from a depth profile generated from backscattered electromagnetic energy using range-gated detection windows.

In various law enforcement and/or military applications, there is a need to determine the presence of certain objects such as contraband, explosives, etc., which may be concealed from view within or by various obscurants, such as a container, a backpack, a garbage can, a box, a wall or other concealing structure, etc. In some instances, the concealed objects have been known to be stored or concealed within a person, either by ingesting the item or by surgically implanting and/or injecting the item underneath the skin. Most methods of volume interrogation are suited to a laboratory environment, where the interrogator is able to move the object to a location with respect to the incident beam and wherein a source and detector may be placed at arbitrary locations and standoffs. However, for explosive material in a field of combat or civilian location, the interrogator does not have these abilities. Bringing the test equipment close to a suspected explosive opens up the possibility of having an explosion destroy the testing equipment or harm the interrogator. Additionally, explosives and other contraband are generally hidden in locations at which there is little possibility of safely placing a beam source and detector on opposite sides of the volume. Methods for testing for such objects outside of a laboratory therefore must address such obstacles.

SUMMARY

According to one embodiment of the present disclosure, a method of profiling a material composition of a volume includes: directing a pulsed beam, or a plurality of pulsed beams, of electromagnetic energy from a source into the volume; receiving, at a detector or a plurality of detectors with a temporal response providing a desired range gate depth resolution, a plurality of backscattered beams generated from a plurality of depths within the volume in response to interactions of the directed pulsed beam at the plurality of depths; performing range gating of the plurality of backscattered beams to obtain a depth profile of backscattered intensity within the volume; and profiling the material composition of the volume from the generated depth profile.

According to another embodiment of the present disclosure, an apparatus for profiling a material composition of a volume includes: a beam source configured to transmit a pulsed electromagnetic beam into the volume; a detector or a plurality of detectors with temporal response providing a desired range gate depth resolution and configured to receive a plurality of backscattered beams generated from a plurality of depths within the volume in response to interactions of the pulsed beam at the plurality of depths; and a processor configured to: perform range gating of the plurality of backscattered beams to obtain a depth profile of backscattered intensity within the volume; and profiling the material composition of the volume from the generated depth profile.

According to another embodiment of the present disclosure, a system for profiling a material composition of a volume includes: a beam source configured to transmit a pulsed beam of electromagnetic energy into the volume; a detector of a plurality of detectors with temporal response providing a desired range gate depth resolution and configured to receive a backscattered beam from the volume generated in response to an interaction of the pulsed beam within the volume; a mobile unit configured to a convey at least one of the beam source and the detector and/or the plurality of detectors to a selected location with respect to the volume; and a processor configured to: perform range gating of the plurality of backscattered beams to generate a depth profile of backscattered intensity within the volume; and obtain a depth profile of the material composition of the volume from the generated depth profile.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

A detailed description of one or more embodiments of the disclosed apparatus and method is presented herein by way of exemplification and not limitation with reference to the Figures.

The present invention provides a method and apparatus for determining a presence of a concealed object from a selected standoff distance. The concealed object may include contraband, explosives or explosive material and may be concealed from view by an obscurant. The selected standoff distance may be a distance away from the object or obscurant at which an operator or equipment is considered safe from a possible detonation of the object. The methods of the present invention therefore enable an operator to examine the object and/or obscurant and to determine the presence of the object within the obscurant from a selected distance. The selected distance may be selected for practical reasons, safety reasons, privacy reasons, legal reasons, or pragmatic reasons. For example, a container may be examined for its contents without opening the container when opening the container may be legally interpreted as an invasion of the container owner's rights and/or privacy. In another embodiment, when a large number of containers are to be examined, such as at a dock of a port, it may not be practical to open all of them.

The present invention may also be used to profile a material composition of the volume. Profiling the material composition may refer to determining the composition of materials located at one or more depths within the volume. A determined profile of the material composition (a "depth profile") may be used to indicate a presence of the object within the volume.

Figure 1:
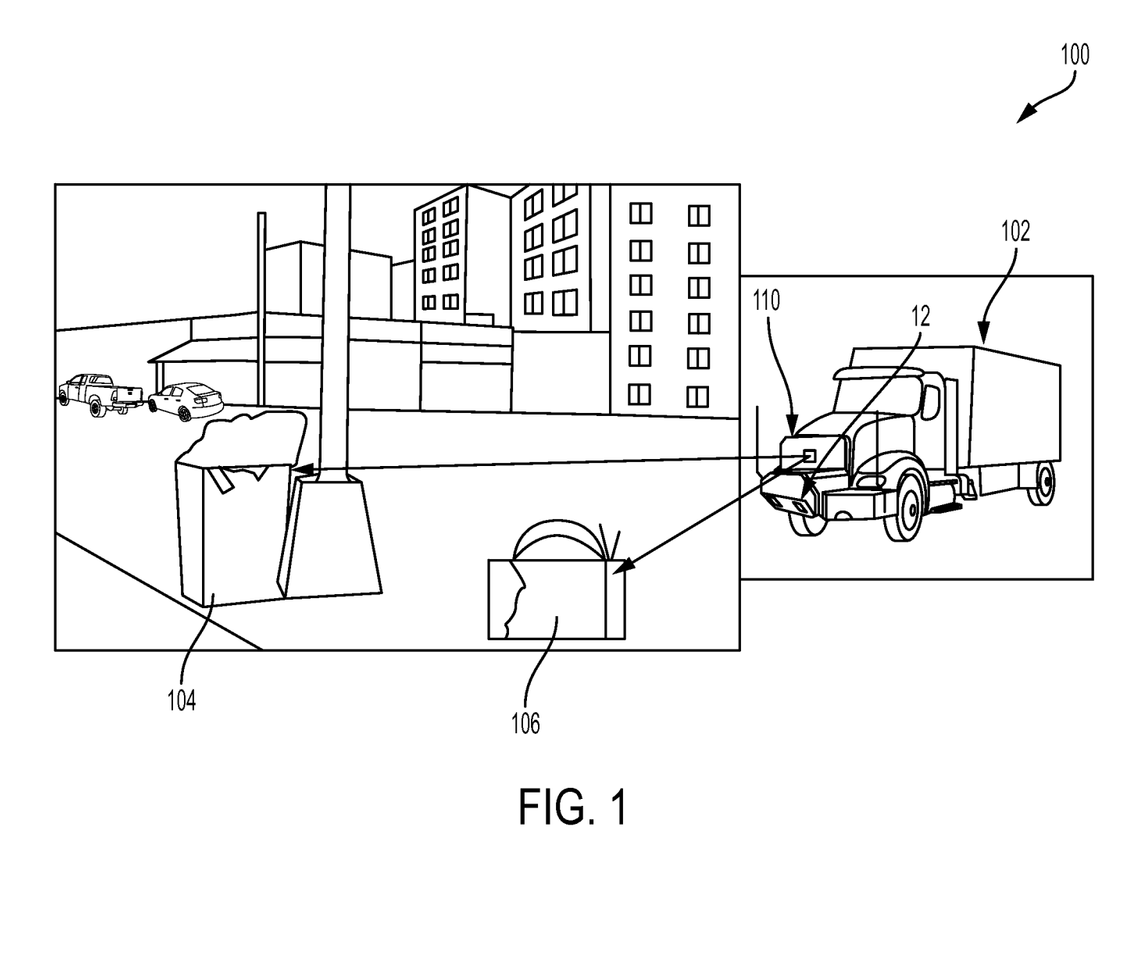
FIG. 1 illustrates an exemplary scenario in which a presence or absence of a concealed object is determined using a testing apparatus in one embodiment.

FIG. 1 illustrates an exemplary scenario 100 in which a presence or absence of a concealed object is determined using a testing apparatus 110 in one embodiment. Mobile unit 102 provides the testing apparatus 110 suitable for determining a presence of the object. The mobile unit 102 may include a vehicle that may be moved, for example, through public spaces, such as city streets, municipalities, country roads, battlefields, etc. In one embodiment, the mobile unit 102 may be driven by a person. In another embodiment, the mobile unit 102 may be a remotely controlled vehicle. The mobile unit 102 transports the testing apparatus 110 to a selected location of an item that is suspected of being an obscurant concealing an object from view. Alternatively, the mobile unit 102 may convey one of a source and a detector of the testing apparatus 110, while another mobile unit (not shown) may convey the other of the source and the detector. In this embodiment, the source and the detector may be moved independently of each another based on situational conditions or demands. FIG. 1 shows illustrative obscurants such as garbage can 104 and/or a backpack 106. However, the obscurant may also be any number of different objects such as for example, a suitcase, a wall, a container, etc. Once the mobile unit 102 is at the location of the obscurant and/or at a selected standoff distance from the obscurant, an operator of the mobile unit 102 may operate the testing apparatus 110 to determine the presence or absence of an object inside or within the obscurant or hidden from view by the obscurant. The testing apparatus 110 may determine the presence of the concealed object while at a non-contact proximity position. The non-contact position may be several millimeters, several centimeters, several meters, hundreds of meters or a kilometer or more from the obscurant, according to various embodiments. In one embodiment, the testing apparatus may direct an electromagnetic beam towards the obscurant from a single location. In another embodiment, the motion device 112 may move the testing apparatus 110 in a selected pattern, such as a raster pattern, to increase a resolution of an object concealed by the obscurant. Operation of the testing apparatus 110 is discussed below with respect to FIGS. 2-6.

Figure 2:
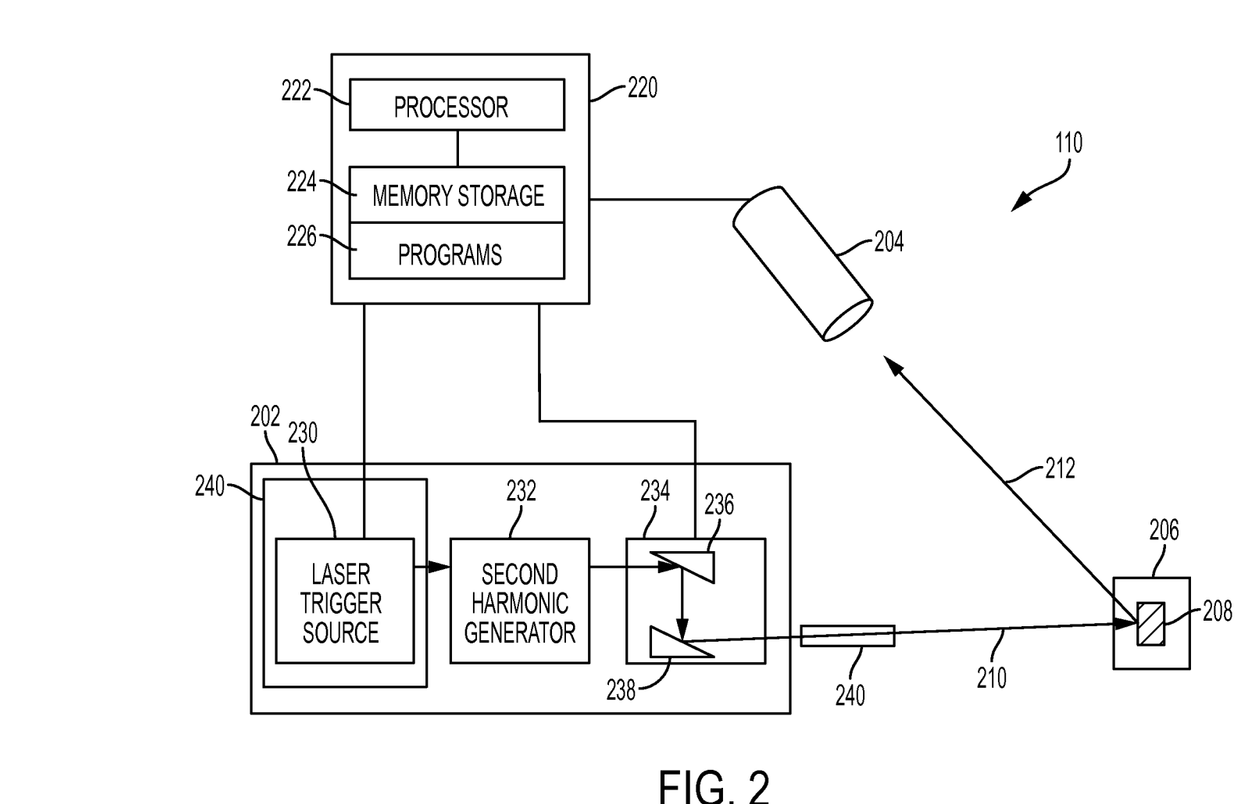
FIG. 2 shows a detailed view of the testing apparatus of FIG. 1 in one embodiment.

FIG. 2 shows a detailed view of the testing apparatus 110 of FIG. 1 in one embodiment. The testing apparatus 110 includes a beam source 202 that generates a beam (referred to herein as "incident beam 210") of electromagnetic energy. The incident beam 210 may be directed towards the obscurant 206 and is incident on the obscurant 206. In various embodiments, the incident beam 210 may include a pulsed beam. The incident beam 210 of electromagnetic energy is capable of penetrating through the material of the obscurant 206. The incident beam 210 interacts with the material of the obscurant 206 as well as with an object 208 that may be within the volume defined by the obscurant 206 to produce one or more backscattered beams 212. The one or more backscattered beams 212 are generally directed towards detector 204. The detector 204 generates signals in response to receiving the one or more backscattered beam 212 and sends the generated signals to a control unit 220. The generated signal may be voltage signal, current signal, power signal, etc. The control unit 220 determines a presence (or absence) of a concealed item 208 within the obscurant 206 from the signals received from the detector 504. The beam source 202 and the detector 204 may be at substantially a same side of the obscurant 206. In various embodiments, the term "backscattered" may refer to all mechanisms of back-directing or otherwise redirecting an incident beam of electromagnetic radiation including, but not limited to, reflection, diffraction, refraction, Mie scattering, Rayleigh scattering, fluorescence, etc.

Beam source 202 may include an X-ray device 234 that is triggered by a laser trigger source 230. Laser-triggered X-ray devices are known in the art. However, other devices for generating X-rays may be used as the X-ray device 234, including devices that trigger X-rays using non-optical methods, such as free-electron lasers, etc. In various embodiments, the laser trigger source 230 generates a plurality of optical pulses having duration within a desired time range. In one embodiment, the pulse duration may be several picoseconds. In another embodiment, the pulse duration may be as short as several femtoseconds. A pulse duration of about 50 picoseconds may provide a centimeter-range resolution, while a pulse duration of several femtoseconds may provide a millimeter-range resolution. The temperature of the laser trigger source 230 may be controlled by a temperature control unit 240 or a suitable laser chilling system. The optical pulses from the laser trigger source 230 may be sent through a second harmonic generator 232 to obtain a plurality of optical pulses at a selected frequency. In one embodiment, the second harmonic generator 232 receives the optical pulses from the laser trigger source 230 and outputs optical pulses at a frequency of about 400 nanometers (nm).

The plurality of optical pulses emanating from the second harmonic generator 232 is incident on photocathode 236 of X-ray device 234. The photocathode 236 emits photoelectrons upon absorption of the energy of the incident optical pulses, thereby converting optical pulses to a pulse of electrons. The generated electrons are then accelerated from the photocathode 236 towards an anode 238 via an applied voltage potential between the photocathode 236 and the anode 238. In various embodiments, the anode 238 is made of heavy metals such as Tungsten (W), Molybdenum (Mo), Tantalum (Ta), etc. In one embodiment, the applied voltage potential may be in a range from about 40 kV to about 300 kV. However, any range of the applied voltage potential may be used in alternate embodiments. The photoelectrons incident on the anode 238 generate X-rays. The X-rays are directed at the obscurant 206 in the form of the incident beam 210. In one embodiment, the incident beam 210 has a pulse width or pulse duration ranging from about 0.1 picoseconds to about 100 picoseconds. However, any range of the pulse width or pulse duration may be used in alternate embodiments. A pulse repetition frequency (PRF) of 1 kilohertz may be used in one embodiment. However, in various embodiments, the PRF may be of any desired range including a range of 1 kHz or higher. A collimator 240 may be used to reduce a divergence of the incident beam 210 leaving the beam source 202.

Conversion at the X-ray device 234 of laser pulses to X-ray pulses may result in pulse stretching of up to two orders of magnitude. Therefore, in order to obtain X-ray pulses having a pulse duration of about 1 picosecond, the laser trigger source 230 may be a femtosecond laser. Laser trigger sources 230 having pulses of duration less than 10 picoseconds are available in the short infrared frequency range to the ultraviolet frequency range. The range-gated three-dimensional imaging device of the present invention includes a source having a short pulse format/waveform capability. Any method or device (other than opticallytriggered X-rays described above) for achieving the desired pulse durations/waveform properties indicated herein may be used for the purposes of the present invention.

While the exemplary beam source 202 shown in FIG. 2 is capable of generating X-rays, in other embodiments, the beam source may suitable for generating an incident beam 210 of electromagnetic energy in a selected energy range that may include, for example, Ka band RF energy, X-rays, gamma rays, ultra-violet, visible, infrared, terahertz frequencies, millimeter wave (mmW) frequencies, etc. The incident beam 212 may have a single frequency (i.e., a monochromatic laser pulse) or may have a range of frequencies (i.e., a broad band X-ray pulse covering a range of photon energies). In general, a pulse width defines a limit of depth resolution that may be obtained.

Detector 204 has a resolution sufficient to resolve backscattered pulses from the obscurant 206. Therefore, in various embodiments, the detector 204 is capable of resolving pulses having sub-nanosecond pulse duration. In one embodiment, detector 204 has a response time in a range from about 50 picoseconds to about 100 picoseconds. In one embodiment, a silicon-based detector may be used as detector 204 to obtain response times in a range from about 50 picoseconds to about 100 picoseconds for an energy range of less than about 30 keV. In another embodiment, a mercury cadmium telluride detector may be used as detector 204 to obtain response times of about 1 nanosecond (ns) for an energy range of greater than about 60 keV. For the methods disclosed herein, detector 204 may use range-gating methods to detect the back-scattered X-rays. The detector 204 may use a method of temporal range-gating, as discussed below with respect to FIGS. 3 and 4.

The testing apparatus 110 is configured to provide a resolution of about 1 cm in depth. However, a testing apparatus having any resolution may be used. For example, testing apparatus 110 may provide a resolution of about 1 mm in depth in alternate embodiments. In order to provide the resolution of about 1 centimeter (cm) in depth, beam source 502 provides a pulse having a duration of less than about 67 picoseconds. Additionally, detector 504 provides range gating windows of commensurate duration.

Control unit 220 may include processor 222, a memory storage device 224 accessible to the processor 222 and a set of programs 226. The set of programs 226 may be stored within the memory storage device 224. The memory storage device 224 may be a non-transitory computer-readable medium such as a solid state memory device, etc. The processor 222 may access the set of programs 226 in order to perform various aspects of the present invention. In one aspect, the controller 220 may control the various operational parameters of the beam source 202 in order to generate the incident beam 210, as discussed below. The controller 220 may further control operation of the detector 504. Furthermore, the processor 220 may generate a suitable graph, image, or text indicative of the presence or absence of the selected material 208 within the obscurant 206. The suitable graph, image or text may be viewed at display 228 by an operator.

The control unit 220 controls various aspects of the source, such as a power of the laser trigger source 230, cooling of the laser trigger source 230, laser pulse duration, laser frequency, laser energy, PRF, etc. The controller 220 may further control aspects of the X-ray device 234 such as including power requirements, voltage potential between photocathode 236 and anode 238. Additionally, the control unit 220 may control various range gating parameters of the detector 504.

Figure 3:
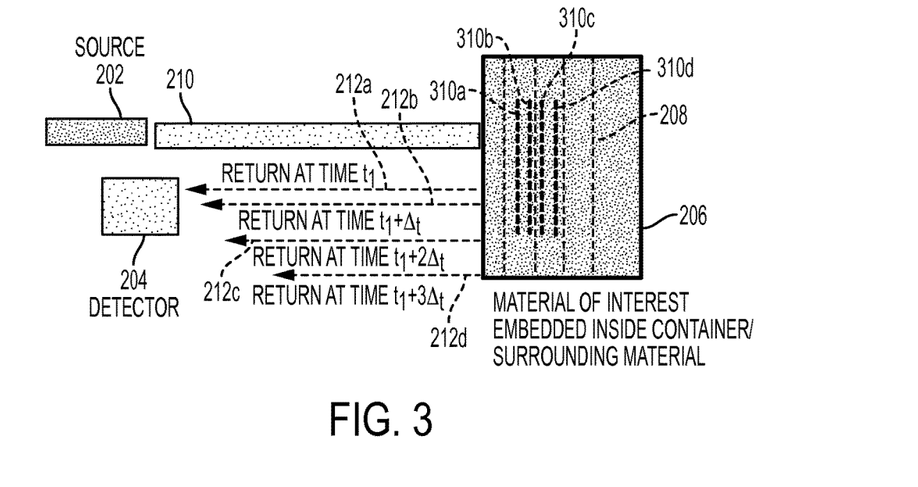
FIG. 3 illustrates a method of backscattering an incident beam from a obscurant by for determining a presence of a concealed item in the obscurant.

FIG. 3 illustrates a method of backscattering an incident beam from an obscurant for determining a presence of a concealed item in the obscurant. FIG. 3 shows the beam source 202 and detector 204 of the detector apparatus of FIG. 2. Obscurant 206 is shown having concealed item 208 embedded within. The incident beam 210 penetrates into obscurant 206 through various depths. While propagating through the obscurant 206, the incident beam 210 interacts with the obscurant 206 at a plurality of depths or layers (310a, 310b, 310c, 310d) of the obscurant 206. In one embodiment, the incident beam 210 interacts with all of the depths or layers of the obscurant 206. While four layers (310a, 310b, 310c, 310d) are shown for illustrative purposes, it is understood that there may be any number of backscattering layers within obscurant 206. At each layer (310a, 310b, 310c, 310d) a backscattered pulse is produced that is representative of the material or composition of the obscurant 206 at each of the plurality of depths. The layers 310a-d may produce distributed back-scattered pulses, fluorescent pulses or other pulses generated by interaction of the incident beam 210 and the layers 310a-d. For example, incident beam 210 interacts with obscurant 206 at depth 310a to produce backscattered pulse 212a. Similarly, incident pulse 212 interacts with obscurant 206 at depth 310b to produce backscattered pulse 212b and at depth 310c to produce backscattered pulse 212c. A travel time may be defined as a difference between a time at which the incident beam 210 is generated at the beam source 202 and a time at which a corresponding backscattered pulse (212a, 212b, 212c, etc.) is received at the detector 204. As shown in FIG. 3, a travel time for backscattered pulse 212a is indicated as $t_1$. Similarly, a travel time of backscattered pulse 212b is $t_1+\Delta t$, where $\Delta t$ is related to a distance between layers 310a and 310b by the speed of light propagation speed in the obscurant 206. "Propagation speed" may also include a speed in a medium between the target and the detector, which could be a vacuum, a liquid, or other medium. A travel time for a backscattered pulse 212c (at depth 310c) is $t_1+2\Delta t$, and a travel time for a backscattered pulse 212d (at depth 310d) is $t_1+3\Delta t$, etc.

Figure 4:
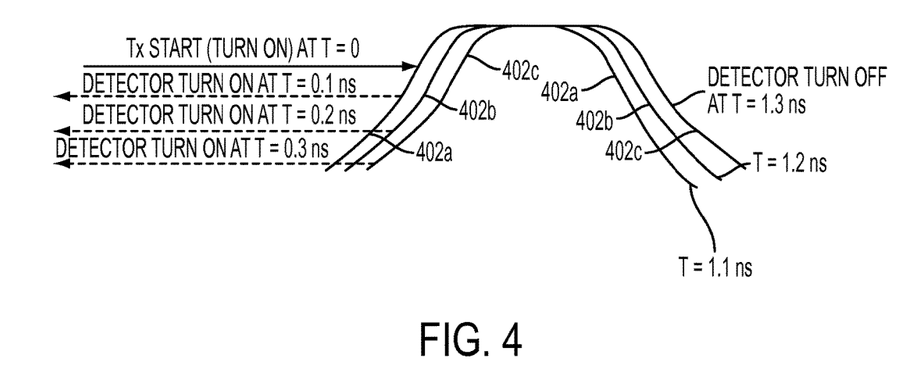
FIG. 4 illustrates an exemplary implementation of range gating at the detector in an exemplary embodiment.

FIG. 4 illustrates an exemplary implementation of range gating at the detector 204 in an exemplary embodiment. Time T=0 indicates a start time of the incident pulse. During a test sequence an incident beam 210 is generated at the beam source 202 and a backscattered pulse 212 is received at the detector 204. During a first sequence, the detector 204 may be turned on at a first time, indicated in FIG. 3 as T=0.1 nanoseconds (T=0.1 ns). The detector 204 is turned off at a later time, indicated in FIG. 3 as T=1.1 ns. Thus, the detecting window 402a (or response time window) for the first test sequence has a duration of about 1.0 ns. During a second sequence, the detector 204 may be turned on at a second time indicated in FIG. 3 as T=0.2 ns and is turned off at T=1.2 ns. Therefore, the detecting window 402b for the second test sequence has a duration time of about 1.0 ns. During a third sequence, a third detecting window 402c may be turned on at a third time (T=0.3 ns) and turned off at T=1.3 ns for a duration time of the detecting window 402c of about 1.0 ns. Thus, the time durations of the detecting windows (402a, 402b, 402c) are substantially equal. In alternative embodiments, the detecting windows 402a-c may have durations that are in a range of about 0.01 ns to about 0.1 ns, depending on specific needs. End times of the detecting windows 402a-c may be governed by a turn off time of the detector readout, which may be as long as several nanoseconds. As is shown in FIG. 4, the detecting windows 402a-c may be partially overlapping. The turn-on times, turn-off times, and durations of the detecting windows (402a, 402b, 402c) can be any value consistent with a particular embodiment or desired resolution. Additionally, the durations of the detecting windows (402a, 402b, 402c) may be different durations.

Figure 5:
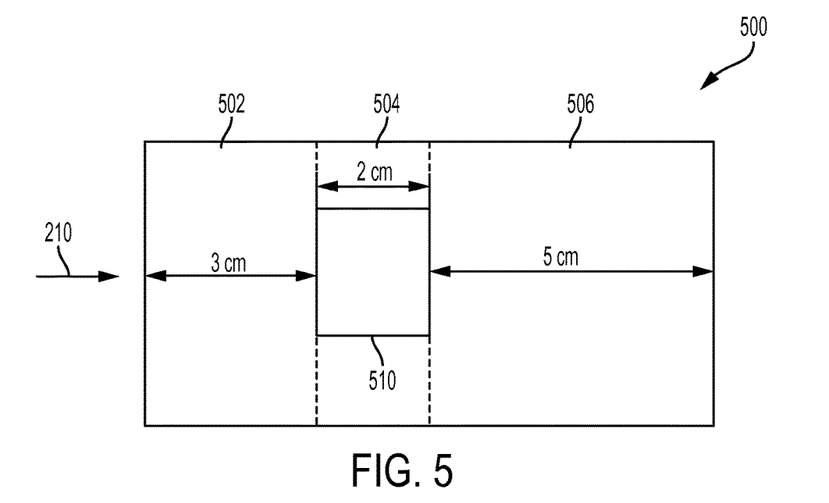
FIG. 5 shows a volume illustrative of an obscurant having an object concealed therein.

FIG. 5 shows a volume 500 illustrative of an obscurant having an object 510 concealed therein. The volume 500 may simulate, for example, contraband material surgically embedded within human tissue. The illustrative volume 500 is 10 centimeters (cm) thick and includes a first layer 502 having a thickness of about 3 centimeters (cm) and containing a gel that simulates human tissue. In one embodiment, the gel may be human tissue or a gel that simulates the characteristics of human tissue. The first layer 502 is adjacent to a second layer 504 having a thickness of about 2 cm. The second layer 504 includes the object 510. The second layer 504 may also include the same gel used in the first layer 502. Thus, the second layer 504 may include both the object 510 as well as the same gel used in the first layer 502. The second layer 504 is adjacent to a third layer 506 having a thickness of about 5 cm and that includes the same gel as in the first layer 502. Additionally, a reference volume may be defined in which all three layers 502, 504, and 506 may include the gel that simulates human tissue, i.e., a "blank volume" devoid of any object 510. In an exemplary embodiment, incident beam 210 is incident on the first layer 502 along a line of propagation extending horizontally from the first layer 502 to the third layer 506.

Figure 6:
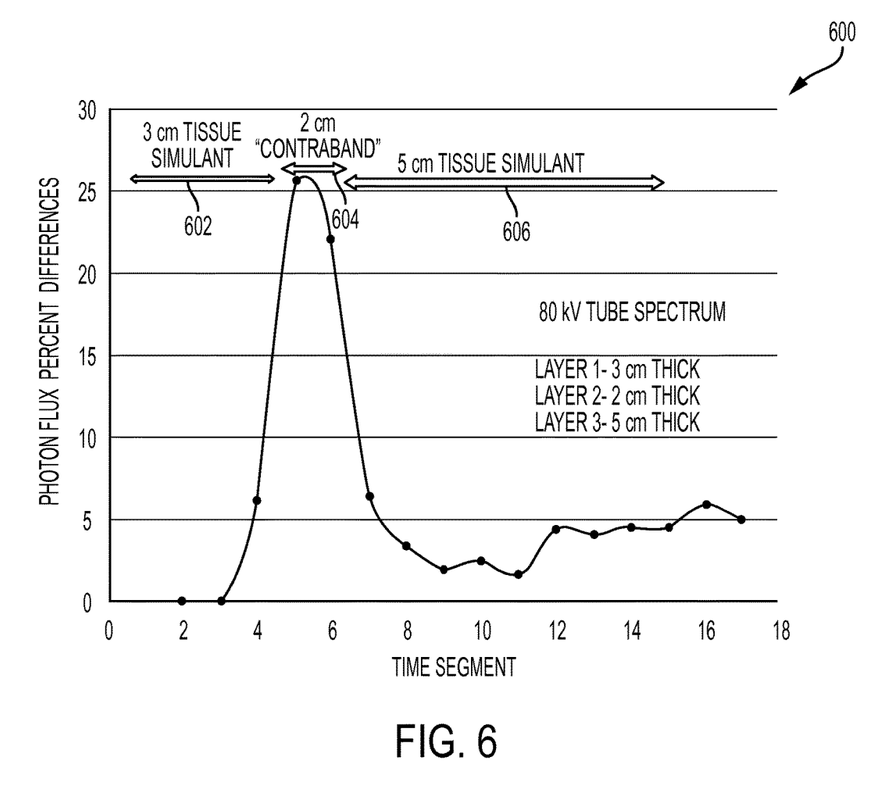
FIG. 6 shows a depth profile obtained from the volume of FIG. 5 using the range-gating methods of FIGS. 3 and 4.

FIG. 6 shows a depth profile 600 calculated from the volume of FIG. 5 using the range-gating methods discussed with respect to FIGS. 3 and 4. The calculations are based on use of a detector having window durations of about 100 picoseconds. The depth profile 600 is calculated using MCNPX (Monte Carlo N-Particle eXtended) modeling software. The depth profile 600 is constructed by calculating the photon flux backscattered from a three-layer volume 500 that includes a contraband layer 504 and comparing this photon flux to a photon flux related to backscattering from a reference volume (i.e., a blank volume) in which all three layers (502, 504, 506) include only the tissue simulant (i.e., the gel) and no object. The comparison is expressed as photon flux percent differences between the target volume containing the object and the reference volume. The photon flux differences are shown along an ordinate axis, and time segments are shown along an abscissa. Being a range gated depth profile, the time segments correspond to depth into the volume 500. For a first time segment 602 (from 0 ns to about 4 ns), the backscattered signal corresponds to the first layer 502 in the volume 500. In both the target volume containing the object and in the reference volume containing no object, the first layer 502 is tissue simulant (gel). With the first layers of both the target and reference volumes being of identical composition, the backscattered photon flux from the respective first layer is the same. Therefore, the percent difference in the photon flux backscattered from the respective first layers is substantially zero, as shown in the first time segment 602. The second time segment 604 (from about 4 ns to about 7 ns) corresponds to the second layer 504. In the target volume, layer 504 includes the object, but in the reference volume, layer 504 is tissue simulant (gel). The second time segment 604 shows that the photon flux backscattered from the second layer 504 of the target volume is 25% greater than the photon flux backscattered from the second layer of the reference volume. A third time segment 606 (from about 7 ns to about 18 ns) corresponds to the third layer 506 of the volume. The signal is the third time segment 606 represents backscattering of the incident pulse from the third layer 506. The processor (222, FIG. 1) may differentiate the signal of the second time segment 604 from the signals of the first time segment 602 and the third time segment 606 to determine that object 510 is embedded within volume 500. In addition, the processor 222 may combine the determined depth profile 600 with a two-dimensional X-ray image obtained via another process in order to obtain a suitable image of the concealed object.

Therefore, in one aspect of the present disclosure, a method of profiling a material composition of a volume includes: directing a pulsed beam of electromagnetic energy from a source into the volume; receiving, at a detector, a plurality of backscattered beams generated from a plurality of depths within the volume in response to interactions of the directed pulsed beam at the plurality of depths; performing range gating of the plurality of backscattered beams to obtain a depth profile of backscattered intensity within the volume; and profiling the material composition of the volume from the generated depth profile. For an object contained within the volume, a presence of the object within the volume may be determined from the profiled material composition of the volume. Alternatively, a material composition of the object within the volume may be determined from the generated depth profile. In one embodiment, performing range gating includes detecting the plurality of backscattered beams using at least a first response time window and a second response time window, wherein a start time of the first response time window is different than a start time of the second response time window and/or a time duration of the first response time window is the same as a duration of the second response time window. In another embodiment, the duration of the first window may be different than the duration of the second window. A response time of the detector may be selected so as to achieve a desired depth resolution. In one embodiment, a response time of the detector may be less than about 100 picoseconds. In various embodiments, the pulse width of the generated pulse beam may be less than about 60 picoseconds and/or capable of providing a depth resolution of less than or equal to one centimeter. Alternately, the pulse width of the generated pulse beam may be capable of providing a depth resolution of greater than one centimeter. The pulsed beam is generated by directing an optical trigger onto a cathode of an X-ray device. A pulse width of the optical trigger pulse is selected to produce an x-ray pulse at the X-ray device suitable for obtaining a desired depth resolution of the volume. In one embodiment, at least one of the source and the detector may be conveyed on a mobile device to a selected standoff distance from the volume. An energy range of the pulse beam may be at least one of: (i) Ka band RF energy; (ii) X-ray energy; (iii) gamma ray energy; (iv) ultra-violet energy; (v) visible light energy; (vi) infrared energy; (vii) an energy for terahertz frequencies; and (viii) and energy for millimeter wave (mmW) frequencies. Depth profiles may be obtained at plurality of locations across a two-dimensional area on the surface of the volume, or alternatively, across a two-dimensional area within the volume, to yield a three-dimensional profile of the volume.

In another aspect of the disclosure, an apparatus for profiling a material composition of a volume includes: a beam source configured to transmit a pulsed electromagnetic beam into the volume; a detector configured to receive a plurality of backscattered beams generated from a plurality of depths within the volume in response to interactions of the pulsed beam at the plurality of depths; and a processor configured to: perform range gating of the plurality of backscattered beams to obtain a depth profile of backscattered intensity within the volume; and profiling the material composition of the volume from the generated depth profile. For an object within the volume, the processor may determine a presence of the object within the volume from the profiled material composition of the volume. Alternatively and/or additionally, the processor may determine a material composition of the object within the volume from the generated depth profile. In one embodiment, the processor is configured to perform the range gating by detecting the backscattered beams using at least a first response time window and a second response time window, wherein a start time of the first response time window is different than a start time of the second response time window and/or a time duration of the first response time window is the same as a duration of the second response time window. In another embodiment, the duration of the first window may be different than the duration of the second window. A response time of the detector may be selected for obtaining a desired depth resolution. In one embodiment, a response time of the detector may be less than about 100 picoseconds. In various embodiments, the pulse width of the generated pulse beam may be less than about 60 picoseconds and/or capable of providing a depth resolution of less than or equal to one centimeter. Alternately, the pulse width of the generated pulse beam may be capable of providing a depth resolution of greater than one centimeter. In one embodiment, the pulsed beam is generated by directing an optical trigger, onto a cathode of an X-ray device. A pulse width of the optical trigger pulse is selected to produce an x-ray pulse at the X-ray device so as to obtain a desired depth resolution of the volume. It is to be noted that the disclosed invention is not limited to optical triggering of a beam pulse and other methods for generating a pulsed beam may be used in other embodiments. In one embodiment, at least one of the source and the detector is configured to be conveyed on a mobile device to a selected standoff distance from the volume. During testing or profiling of the volume, the detector may be located at one of: (i) substantially at a same side of the volume as the source; and (ii) at a location with respect to the volume substantially opposite the source.

In yet another aspect of the disclosure, a system for profiling a material composition of a volume includes: a beam source configured to transmit a pulsed beam of electromagnetic energy into the volume; a detector configured to receive a backscattered beam from the volume generated in response to an interaction of the pulsed beam within the volume; a mobile unit configured to a convey at least one of the beam source and the detector to a selected location with respect to the volume; and a processor configured to: perform range gating of the plurality of backscattered beams to generate a depth profile of backscattered intensity within the volume; and estimate material composition of the volume at a plurality of depths of the volume from the generated depth profile. For an object within the volume, the processor may determine a presence of the object within the volume may be determined from the profiled material composition of the volume. Alternatively, the processor may determine a material composition of the object within the volume from the generated depth profile. In one embodiment, the processor is configured to perform the range gating by detecting the backscattered beams using at least a first response time window and a second response time window, wherein a start time of the first response time window is different than a start time of the second response time window and/or a time duration of the first response time window is the same as a time duration of the second response time window. In another embodiment, the duration of the first window may be different than the duration of the second window. A motion device may be used to move at least one of the source and the detector in a raster pattern.

While the present invention has been discussed with respect to performing range-gating depth profiling along a single axis, it is possible to perform a raster pattern using the incident beam in order to construct a depth profile image at a spatial resolution of the raster pattern.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list or string of at least two terms is intended to mean any term or combination of terms. The term "secure" relates to one component being coupled either directly to another component or indirectly to another component via one or more intermediate components.

While the disclosure has been described with reference to a preferred embodiment or embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A method of profiling a material composition of a volume, comprising:
   directing a pulsed beam of electromagnetic energy from a source into the volume, wherein the volume includes an object and an obscurant;
   receiving, at a detector, a plurality of backscattered beams generated from a plurality of depths within the volume in response to interactions of the directed pulsed beam at the plurality of depths;
   performing range gating of the plurality of backscattered beams to obtain a depth profile of backscattered intensity within the volume; and
   comparing the depth profile of backscattered intensity within the volume to a depth profile of backscattered intensity from a reference volume including only the obscurant to determine a presence of the object within the volume.

2. The method of claim 1, further comprising determining a location of the object within the volume from the comparison of the depth profiles.

3. The method of claim 1, wherein performing range gating further comprises detecting the plurality of backscattered reflected beams using at least a first response time window and a second response time window, wherein at least one of: (i) a start time of the first response time window is different than a start time of the second response time window; (ii) a time duration of the first response time window is the same as a duration of the second response time window; and (iii) a time duration of the first response time window is different than a time duration of the second time window.

4. The method of claim 1, wherein a pulse width of the generated pulse beam is at least one of: (i) less than about 60 picoseconds; (ii) capable of providing a depth resolution of less than or equal to one centimeter; and (iii) capable of providing a depth resolution of greater than one centimeter.

5. The method of claim 1, further comprising selecting a response time of the detector suitable to provide a selected depth resolution of the volume.

6. The method of claim 1, wherein the pulsed beam is generated by directing an optical trigger pulse onto a cathode of an X-ray device, wherein a pulse width of the optical trigger pulse is selected to produce an x-ray pulse at the X-ray device suitable for obtaining a desired depth resolution of the volume.

7. The method of claim 1 further comprising conveying at least one of the source and the detector on a mobile device to a selected standoff distance from the volume.

8. The method of claim 1, wherein an energy range of the pulse beam is at least one of: (i) Ka band RF energy; (ii) X-ray energy; (iii) gamma ray energy; (iv) ultra-violet energy; (v) visible light energy; (vi) infrared energy; (vii) an energy for terahertz frequencies; and (viii) and energy for millimeter wave (mmW) frequencies.

9. The method of claim 1, further comprising obtaining a plurality of depth profiles at at least one of: (i) across a two-dimensional area of a surface of the volume; and (ii) across a two-dimensional area within the volume, to yield a three-dimensional profile of the volume.

10. An apparatus for profiling a material composition of a volume, comprising:
a beam source configured to transmit a pulsed electromagnetic beam into the volume, wherein the volume includes an object and an obscurant;
a detector configured to receive a plurality of backscattered beams generated from a plurality of depths within the volume in response to interactions of the pulsed beam at the plurality of depths; and
a processor configured to:
perform range gating of the plurality of backscattered beams to obtain a depth profile of backscattered intensity within the volume; and
compare the depth profile of backscattered intensity within the volume to a depth profile of backscattered intensity from a reference volume including only the obscurant to determine a presence of the object within the volume.

11. The apparatus of claim 10, wherein the processor is further configured to determine a location of the object within the volume from the comparison of the depth profiles.

12. The apparatus of claim 10, wherein the processor is configured to perform the range gating by detecting the backscattered beams using at least a first response time window and a second response time window, wherein at least one of: (i) a start time of the first response time window is different than a start time of the second response time window; (ii) a time duration of the first response time window is the same as a duration of the second response time window; and (iii) a time duration of the first response time window is different than a time duration of the second time window.

13. The apparatus of claim 10, wherein a pulse width of the generated pulse beam is at least one of: (i) less than about 60 picoseconds; (ii) capable of providing a depth resolution of less than or equal to one centimeter; and (iii) capable of providing a depth resolution of greater than one centimeter.

14. The apparatus of claim 10, wherein the beam source further comprises a laser configured to direct an optical trigger pulse onto a cathode of an X-ray device, wherein a pulse width of the optical trigger pulse is selected to produce an x-ray pulse at the X-ray device suitable for obtaining a desired depth resolution of the volume.

15. The apparatus of claim 10 wherein at least one of the source and the detector is configured to be conveyed on a mobile device to a selected a standoff distance from the volume.

16. The apparatus of claim 10, wherein the detector is one of: (i) substantially at a same side of the volume as the source; and (ii) at a location with respect to the volume substantially opposite the source.

17. A system for profiling a material composition of a volume, comprising;
a beam source configured to transmit a pulsed beam of electromagnetic energy into the volume, wherein the volume includes an object and an obscurant;
a detector configured to receive a backscattered beam from the volume generated in response to an interaction of the pulsed beam within the volume;
a mobile unit configured to a convey at least one of the beam source and the detector to a selected location with respect to the volume; and
a processor configured to:
perform range gating of the plurality of backscattered beams to generate a depth profile of backscattered intensity within the volume, and
compare the depth profile of backscattered intensity within the volume to a depth profile of backscattered intensity from a reference volume including only the obscurant to determine a presence of the object within the volume.

18. The system of claim 17, wherein the processor is further configured to determine a location of the object within the volume from the comparison of the depth profiles.

19. The system of claim 17, wherein the processor is configured to perform the range gating by detecting the backscattered beams using at least a first response time window and a second response time window, wherein at least one of: (i) a start time of the first response time window is different than a start time of the second response time window; (ii) a time duration of the first response time window is the same as a duration of the second response time window and (iii) a time duration of the first response time window is different than a time duration of the second time window.

20. The system of claim 17, further comprising a motion device configured to move at least one of the source and the detector in a raster pattern.

* * * * *